US00PP20390P2

(12) United States Plant Patent
Pieters

(10) Patent No.: US PP20,390 P2
(45) Date of Patent: Oct. 6, 2009

(54) ***CHRYSANTHEMUM MORIFOLIUM* PLANT NAMED 'PPP NAV RD07'**

(50) Latin Name: *Chrysanthemum morifolium*
Varietal Denomination: PPP NAV RD07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,801

(22) Filed: Jul. 18, 2008

(51) Int. Cl.
*A01H 5/00* (2006.01)

(52) U.S. Cl. ..... Plt./293

(58) Field of Classification Search ..... Plt./293
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by small decorative type inflorescences, consistent flowering response to short days, blooming consistently after 49 days of short day length, bronze red ray florets, free branching habit, and a consistent natural season flowering habit during the last week of September.

1 Drawing Sheet

Latin name of the genus and species: *Chrysanthemum morifolium.*

Variety denomination: 'PPP NAV RD07'.

BACKGROUND OF THE INVENTION

The new cultivar 'PPP NAV RD07' is a product of a cross between the male parent 'Medonia Red' (not patented in the United States) and the female parent 'Kingfish' (U.S. Plant Pat. No. 11,497). The new cultivar was discovered and selected by Dirk Pieters in September of 2004 in Oostnieuwkerke, Belgium.

Asexual reproduction of the new cultivar 'PPP NAV RD07' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP NAV RD07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP NAV RD07.' These characteristics in combination distinguish 'PPP NAV RD07' as a new and distinct *Chrysanthemum* cultivar:

1. Small, dark red, decorative-type inflorescences;
2. Free branching habit;
3. Consistent natural season flowering habit during the last week of September; and
4. Consistent flowering response to short days, blooming consistently after 49 days of short day length.

Plants of the new cultivar 'PPP NAV RD07' are similar to plants of the male parent variety, 'Medonia Red' in most horticultural characteristics, however plants of the new cultivar 'PPP NAV RD07' are shorter. Also, the new cultivar 'PPP NAV RD07' has a bigger inflorescence diameter. Additionally, the ray florets of 'PPP NAV RD07' are more bronze red compared to the true red of the ray florets of the male parent. Finally, 'PPP NAV RD07' naturally blooms two weeks earlier than the male parent 'Medonia Red.'

Plants of the new cultivar 'PPP NAV RD07' are similar to plants of the female parent variety, 'Kingfish' in most horticultural characteristics, however plants of the new cultivar 'PPP NAV RD07' are shorter. Also, the new cultivar 'PPP NAV RD07' has a smaller, dark red inflorescence, compared to the larger orange/yellow bicolor inflorescence of the female parent. Additionally, 'Kingfish' has more inflorescences per lateral branch than 'PPP NAV RD07'. Finally, 'PPP NAV RD07' has a different inflorescence type than the female parent.

In comparison to the commercially available variety 'GEDI ONE GAL' (U.S. Plant Pat. No. 13,807), 'PPP NAV RD07' is smaller in both height and plant spread. Additionally, the comparable variety 'GEDI ONE GAL' has more inflorescences per lateral branch and a wider inflorescence diameter than the new variety 'PPP NAV RD07'. Further, the ray florets of the new variety 'PPP NAV RD07' are a bronze red with a bright yellow base compared to the pure red-purple ray florets of 'GEDI ONE GAL'. Finally, the new cultivar 'PPP NAV RD07' has longer inflorescence longevity.

BRIEF DESCRIPTION OF THE PHOTOGRAPH

The accompanying photograph illustrates in full color a typical plant of 'PPP NAV RD07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP NAV RD07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP NAV RD07.'

Commercial classification: Garden-type *Chrysanthemum.*

PROPAGATION

Time to rooting: 7 to 14 days at approximately 21° C.

Root description: Fine, fibrous.

PLANT

Growth habit: Mounding herbaceous perennial.

Height: Approximately 17 cm.

Plant spread: Approximately 30 cm.

Growth rate: Moderate.

Branching characteristics: Free Branching.

Length of lateral branches: Approximately 10 cm.

Number of leaves per lateral branch: Approximately 20.

Age of plant described: Approximately 150 days.

FOLIAGE

Leaf:

*Arrangement.*—Alternate single.

*Average length.*—Approximately 2.5 cm.

*Average width.*—Approximately 1.75 cm.

*Shape of blade.*—Ovate.

*Apex.*—Acuminate.

*Base.*—Attenuate.

*Attachment.*—Stalked.

*Margin.*—Serrate.

*Texture of top surface.*—Lightly pubescent.

*Texture of bottom surface.*—Lightly pubescent.

*Leaf internode length.*—Approximately 0.8 cm.

*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.

*Venation.*—Type: Palmately net. Venation color upper side: Near Yellow-Green 147C. Venation color under side: Near Yellow-Green 147C.

Petiole:

*Average length.*—Approximately 0.75 cm.

*Color.*—Near Yellow-Green 147C.

*Diameter.*—Approximately 0.2 cm.

BLOOM

Inflorescence:

*Flowering habit.*—Induced by darkness period greater than 13.5 hours, approximately 49 days of appropriate day length required to induce and develop blooms.

*Inflorescence form.*—Decorative.

*Natural flowering season.*—Approximately the last week of September.

*Number of inflorescences per lateral branch.*—Approximately 8.

*Inflorescence diameter.*—Approximately 3.3 cm.

*Inflorescence depth.*—Approximately 1.5 cm.

*Inflorescence longevity on plant.*—Approximately 28 to 34 days.

*Persistence.*—Persistent.

Ray florets:

*Appearance.*—Matte.

*Texture.*—Smooth.

*Average number of ray florets per inflorescence.*—160.

*Shape.*—Oblanceolate.

*Aspect.*—Flat.

*Margin.*—Entire.

*Apex.*—Obtuse.

*Length.*—Approximately 1.1 cm.

*Width.*—Approximately 0.4 cm.

*Color.*—Upper surface at first opening: Near Greyed-Purple 185A with near Yellow 12A base. Upper surface at maturity: Near Greyed-Red 181A with a near Yellow 12A base. Upper surface at fading: Near Greyed-Red 180A with near Yellow 12B base. Under surface at first opening: Near Greyed-Purple 185A with near Yellow 12A base. Under surface at maturity: Near Greyed-Red 181 B with near Yellow 12A base. Under surface at fading: Near Greyed-Red 181C with near Yellow 12B base.

Disc florets:

*Appearance.*—Shiny.

*Texture.*—Smooth.

*Average number of florets per disc.*—Approximately 43.

*Shape.*—Cylindric.

*Apex.*—Obtuse.

*Average length.*—Approximately 0.4 cm.

*Average width.*—Approximately 0.1 cm.

*Color.*—At first opening: Near Yellow 12A. At maturity: Near Yellow 12A. At fading: Near Yellow 12B.

Peduncle:

*Length.*—At terminal end (shortest): Approximately 2 cm. At lateral end (longest): Approximately 7.8 cm.

*Angle to stem.*—Acute.

*Strength.*—Moderate.

*Color.*—Near Green 138B.

*Habit.*—Upright.

*Diameter.*—Approximately 0.3 cm.

*Surface texture.*—Lightly pubescent.

Inflorescence bud:

*Length.*—Approximately 1.2 cm.

*Diameter.*—Approximately 0.8 cm.

*Form.*—Globular.

*Color.*—Near Greyed-Purple 185A.

Involucral bracts (phyllaries):

*Appearance.*—Matte.

*Texture.*—Lightly pubescent.

*Number.*—Approximately 30.

*Shape.*—Ovate.

*Margin.*—Entire.

*Apex.*—Acute.

*Length.*—Approximately 0.5 cm.

*Width.*—Approximately 0.2 cm.

*Color.*—Upper side: Near Green 138A. Under side: Near Green 138B.

REPRODUCTIVE ORGANS

Ray florets:

*Number of pistils per floret.*—1.

*Stigma shape.*—2 branched.

*Stigma color.*—Near Yellow 12A.

*Style color.*—Near Green-Yellow 1C.

*Style length.*—Approximately 0.4 cm.

*Stamens.*—Absent.

Disc florets:

*Number of pistils per floret.*—1.
*Stigma shape.*—Cylindric.
*Stigma color.*—Near Yellow 12A.
*Style length.*—Approximately 0.2 cm.
*Style color.*—Near Green-Yellow 1C.
*Number of stamens per floret.*—Approximately 5.
*Anther shape.*—Tubular.
*Anther color.*—Near Yellow 12A.
*Pollen color.*—Near Yellow 12A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP NAV RD07' as herein illustrated and described.

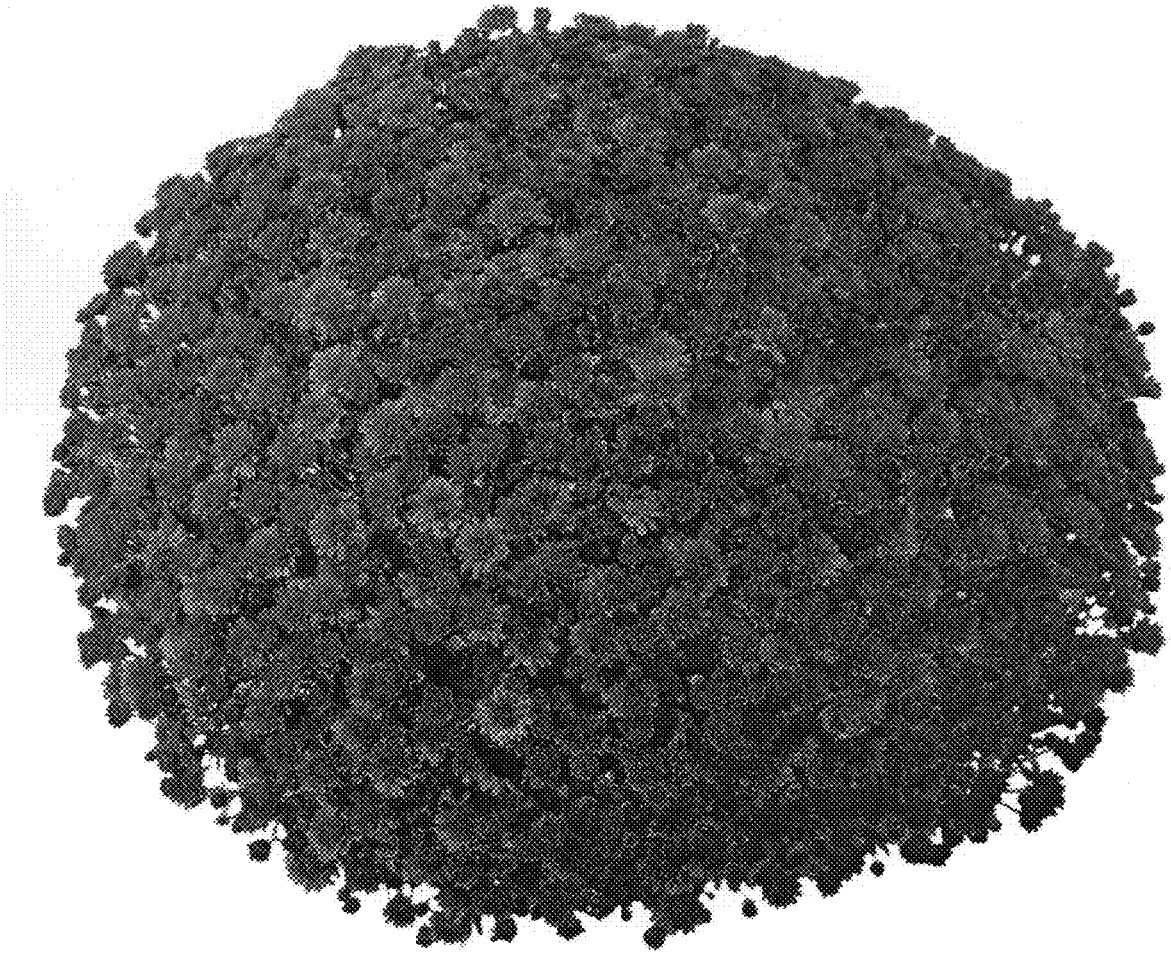

* * * * *